US005686645A

United States Patent [19]

Faraj

[11] Patent Number: 5,686,645
[45] Date of Patent: Nov. 11, 1997

[54] SYNTHESIS OF ISOCYANATE PRECURSORS FROM PRIMARY FORMAMIDES

[75] Inventor: Mahmoud K. Faraj, Newtown Square, Pa.

[73] Assignee: ARCO Chemical Technology, L.P., Greenville, Del.

[21] Appl. No.: 902,615

[22] Filed: Jun. 23, 1992

Related U.S. Application Data

[62] Division of Ser. No. 782,027, Oct. 24, 1991, Pat. No. 5,155,267.

[51] Int. Cl.$^6$ .................. C07C 261/00; C07C 269/00; C07C 271/00
[52] U.S. Cl. .................. 560/24; 560/157; 560/158
[58] Field of Search .................. 560/24, 157, 158

[56] References Cited

U.S. PATENT DOCUMENTS

| 3,960,914 | 6/1976 | Lyons | 260/453 P |
|---|---|---|---|
| 4,097,524 | 6/1978 | Kesling | 564/132 |
| 4,207,251 | 6/1980 | Heyboer | 260/453 |
| 4,537,726 | 8/1985 | Rao et al. | 260/453 P |
| 4,683,329 | 7/1987 | Rao | 560/338 |
| 4,871,871 | 10/1989 | Shawl et al. | 560/344 |
| 4,873,364 | 10/1989 | Shawl et al. | 560/344 |
| 4,883,908 | 11/1989 | Shawl et al. | 560/344 |
| 4,978,779 | 12/1990 | Shawl et al. | 560/344 |

FOREIGN PATENT DOCUMENTS

| 0014103 | 8/1980 | European Pat. Off. | 560/24 |
|---|---|---|---|
| 2908250 | 9/1980 | Germany | 560/24 |

OTHER PUBLICATIONS

J. Chem. Soc., Chem. Commun (1990) 549.

*Primary Examiner*—Keith MacMillan
*Attorney, Agent, or Firm*—Jonathan L. Schuchardt

[57] ABSTRACT

A selective process for the production of unsymmetric carbamates and ureas is disclosed. In the process, a primary formamide is reacted with a dialkyl amine or an alcohol in the presence of a Group VIII transition metal catalyst. The unsymmetric carbamates and ureas are useful precursors to isocyanates.

14 Claims, No Drawings

SYNTHESIS OF ISOCYANATE PRECURSORS FROM PRIMARY FORMAMIDES

This is a division of application Ser. No. 07/782,027, filed Oct. 24, 1991, now U.S. Pat. No. 5,155,267, issued Oct. 13, 1992.

FIELD OF THE INVENTION:

The invention relates to the synthesis of isocyanate precursors from primary formamides. In particular, unsymmetric carbamates or ureas, which may be cracked to give isocyanates, are selectively produced by dehydrogenating a primary formamide in the presence of a dialkyl amine or alcohol.

BACKGROUND OF THE INVENTION:

Commercially important isocyanates such as tuolene diisocyanate (TDI) and methylene diphenylene diisocyanate (MDI) are usually prepared by reacting the corresponding diamines with phosgene. Because of toxicity concerns about phosgene, alternative non-phosgene routes to isocyanates are of interest. One non-phosgene approach to isocyanates is to crack dialkylureas in the presence of various promoters, as is taught in U.S. Pat. Nos. 4,871,871, 4,873,364, 4,883,908, and 4,978,779. Carbamates can also be cracked thermally or in the presence of promoters to give isocyanates. A disadvantage of these processes is that economical, selective routes to the required carbamates or dialkylureas from inexpensive starting materials are lacking, particularly for unsymmetric aromatic carbamates and ureas.

Oxidative dehydroganation of N-methylformamide in the presence of a silver catalyst produces water and methyl isocyanate, as disclosed, for example, in U.S. Pat. Nos. 4,537,726 and 4,683,329. The process is effective for low-boiling isocyanates like methyl isocyanate, but is impractical for synthesis of other useful isocyanates like TDI and MDI because numerous side-products form. For example, U.S. Pat. No. 4,207,251 teaches oxidative dehydrogenation of formamides to produce TDI or HDI, but yields are 27–30%, and side products make the route commercially unattractive.

A conceptually more inviting route to isocyanates from formamides involves dehydrogenation of the amide without oxidation. The reaction products are an isocyanate and gaseous hydrogen rather than an isocyanate and water. Recovery of hydrogen in the isocyanate-forming reaction is a bonus because the hydrogen can be recycled for use in nitro-reduction step that begins the synthesis:

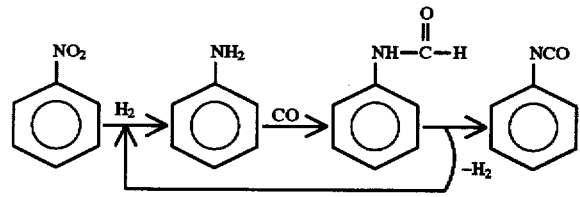

Watanabe et al. (*J. Chem. Soc., Chem. Commun.* (1990) 549) reported a synthesis of N,N'-diphenylurea in 92% yield by dehydrogenating formanilide in the presence of aniline and a ruthenium catalyst:

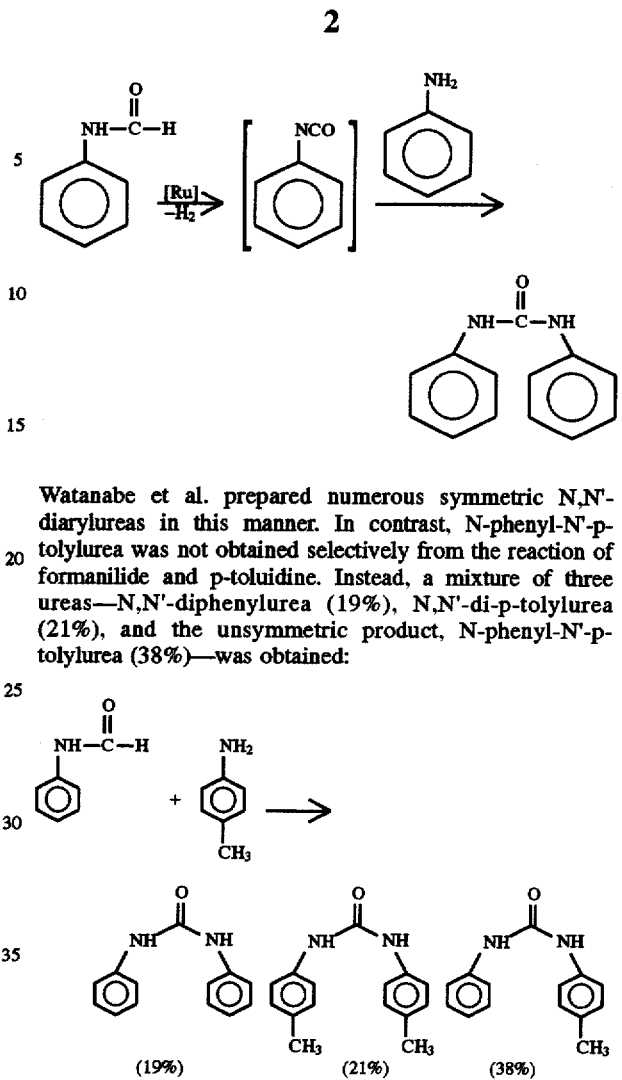

Watanabe et al. prepared numerous symmetric N,N'-diarylureas in this manner. In contrast, N-phenyl-N'-p-tolylurea was not obtained selectively from the reaction of formanilide and p-toluidine. Instead, a mixture of three ureas—N,N'-diphenylurea (19%), N,N'-di-p-tolylurea (21%), and the unsymmetric product, N-phenyl-N'-p-tolylurea (38%)—was obtained:

A selective process for producing unsymmetric carbamates or ureas is needed. Preferably, the ureas or carbamates are ones that can be easily cracked in the presence of a promoter to give isocyanates. Also preferred is a process that produces hydrogen, which can be used at an earlier step in the overall process.

SUMMARY OF THE INVENTION:

The invention is a selective process for making an unsymmetric urea or carbamate. The process comprises reacting a primary formamide with an alcohol or a dialkylamine in the presence of a Group VIII transition metal catalyst at a temperature and for a time sufficient to produce the unsymmetric urea or carbamate. Since the process involves non-oxidative dehydrogenation, it gives useful hydrogen rather than water as a by-product.

DETAILED DESCRIPTION OF THE INVENTION:

In the process of the invention, a primary formamide is reacted with a dialkyl amine or an alcohol to produce an unsymmetric urea or carbamate.

The primary formamides useful in the process of the invention preferably have the general formula:

in which A is a $C_1$–$C_{30}$ linear, branched, or cyclic alkyl, aryl, or aralkyl group, and x is an integer from 1 to 6.

Examples of suitable formamides include, but are not limited to, formamide, N-methylformamide, N-ethylformamide, N-propylformamide, N-isobutylformamide, formanilide, toluene-2,4-bis (formamide), toluene-2,6-bis(formamide), 4,4'-methylene-bis-(4-formamidobenzene), 1,6-bis(formamido)hexane, and the like, and mixtures thereof. Preferred primary formamides include mono-, di-, and polyformamido derivatives of benzene, toluene, diphenylmethane, poly (phenylmethylene), isophorone, and hexane.

Dialkyl amines useful in the process of the invention preferably have the general formula R—NH—R', in which each of R and R' separately represents a $C_1$–$C_{30}$ linear, branched, or cyclic alkyl or aryl-substituted alkyl group. Alternatively, the alkyl groups may form a ring, as in pyrrolidine and piperidine.

Examples of suitable dialkyl amines include, but are not limited to, dimethylamine, diethylamine, dipropylamines, dibutylamines, methylethylamine, n-octylamine, N-methyl-N-benzylamine, N-methyl-N-cyclohexylamine, and the like, and mixtures thereof. Particularly preferred are relatively volatile dialkyl amines such as dimethylamine, diethylamine, diisopropylamine, di-n-butylamine, and the like.

Alcohols, in addition to dialkyl amines, are useful trapping agents in the process of the invention. The alcohol preferably has the structure R"OH in which R" is a $C_1$–$C_{30}$ linear, branched, or cyclic alkyl or aryl-substituted alkyl group.

Examples of suitable alcohols include, but are not limited to, methanol, ethanol, n-propanol, isopropanol, n-butyl alcohol, tert-butyl alcohol, sec-butyl alcohol, n-pentyl alcohol, n-hexyl alcohol, n-octyl alcohol, isoamyl alcohol, cyclohexanol, benzyl alcohol, and the like, and mixtures thereof.

Group VIII transition metal compounds are useful catalysts in the process of the invention. The catalysts contain a metal selected from the group consisting of iron, cobalt, nickel, ruthenium, rhodium, palladium, osmium, iridium, and platinum. Ruthenium compounds are preferred.

The catalyst may be soluble in the reaction medium, may be slurried, or may be supported by any suitable means. For example, the catalyst may be supported on carbon, alumina, silica, or the like, or it may be bonded to a polymeric support such as a poly(styrene-divinylbenzene) or other polymer matrix.

Examples of suitable Group VIII transition metal compounds include, but are not limited to, ruthenium trichloride, dichlororuthenium(II) tris(triphenylphosphine), dichlororuthenium(II) tetrakis(dimethyl sulfoxide), hydridochlororuthenium(II) tris(triphenylphosphine), nickel (0) tetrakis(triphenylphosphine), palladium(0) tetrakis (triphenylphosphine), rhodium trichloride, chlororhodium tris(triphenylphosphine), and the like, and mixtures thereof. Mixed-metal compounds can also be used provided at least one Group VIII transition metal is present.

The process of the invention is performed with or without a solvent present. Any inert organic solvent can be used. Preferred solvents will dissolve the formamide, alcohol or dialkyl amine, and catalyst. Preferred solvents for the process are aromatic hydrocarbons. Examples of suitable solvents include, but are not limited to, toluene, mesitylene, diphenylmethane, phenyldecane, diphenyl ether, hexadecane, and the like. If desired, it is also possible to use the dialkyl amine or alcohol reactant in excess so that it also functions as a solvent.

The process of the invention can be performed at any desired temperature. Typically, elevated temperatures are most satisfactory. Preferably, the reaction temperature is within the range of about 100° C. to about 300° C. More preferred is the range from about 140° C. to about 180° C. The reaction temperature is conveniently controlled by choosing a solvent that has a boiling point close to the desired reaction temperature, and running the reaction in refluxing solvent.

The process of the invention may be performed at, above, or below atmospheric pressure, as desired. When a volatile dialkyl amine such as dimethylamine is used as a starting material, for example, it is typically most convenient to perform the reaction at pressures greater than 1 atmosphere.

Any suitable reaction vessel may be employed. Generally, the reactor must be able to withstand the pressure used, it must resist corrosion by the dialkyl amine, and it must not interfere with catalyst activity.

The process of the invention is preferably performed under an atmosphere of an inert, non-oxidizing gas. Examples of suitable gases include nitrogen, argon, and the like.

The following examples merely illustrate the invention. Those skilled in the art will recognize numerous variations that are within the spirit of the invention and scope of the claims.

EXAMPLE 1

Formanilide (0.48 g) is combined with di-n-butylamine (0.52 g) and mesitylene (10 mL) in a round-bottom flask under an atmosphere of dry nitrogen. Ruthenium dichloride tris(triphenylphosphine) (0.20 g) is added, and the stirred reaction mixture is heated to 165° C. Progress of the reaction is followed by high-performance liquid chromatography (HPLC). After 20 hours, conversion of formanilide is 19% and the products identified are: N,N-di-n-butyl-N'-phenylurea (DBPU) (90%) and N,N'-diphenylurea (DPU) (6%).

EXAMPLE 2

The procedure of Example 1 is followed with diphenylmethane (10 mL) as the solvent. After 20 hours, conversion of formanilide is 50%, and N,N-di-n-butyl-N'-phenylurea (DBPU) is the only observed product (>90%).

EXAMPLE 3

The procedure of Example 2 is followed, except that only 2.5 mL of diphenylmethane is used. After 6 hours, conversion is 75%, and selectivity to DBPU is 85%.

EXAMPLE 4

The procedure of Example 2 is followed with ruthenium dichloride tetrakis(dimethylsulfoxide) as the catalyst (1/40 molar ratio vs. formanilide). After 20 hours, conversion is 55%, and DBPU is the only observed product (>90%).

EXAMPLE 5

The procedure of Example 2 is followed with palladium tetrakis(triphenylphosphine) as the catalyst. After 20 hours, conversion is 54%, and the products are DBPU (25%), DPU (20%), and aniline (40%).

EXAMPLE 6

The procedure of Example 2 is followed with RhCl(CO)(PPh$_3$)$_3$ as the catalyst. After 20 hours, conversion is 18%, and the products are DBPU (10%), DPU (5%), and aniline (65%).

EXAMPLE 7

The procedure of Example 1 is used, except that mesitylene is omitted, and n-hexanol (10 mL) is used in place of di-n-butylamine. After 6 hours, conversion is 90%, and the only observed product is N-phenylhexylcarbamate (50%).

EXAMPLE 8

The procedure of Example 1 is used, except that mesitylene is omitted, n-hexanol (10 mL) is used in place of di-n-butylamine, and toluene-2,4-bisformamide (0.50 g) is used in place of formanilide. After 4 hours, conversion is 78%, and selectivity to toluene-2,4-bis(n-hexylcarbamate) is 20%. The only other products identified were the monocarbamate-monoformamide intermediates.

As shown in Examples 1–6 (Table 1), the reaction of formanilide and dibutylamine using mesitylene or diphenylmethane as a solvent and a Group VIII metal catalyst often gives N-phenyl-N',N'-dibutylurea as the major or only reaction product. Bis(dialkylurea) products are not observed at all, and N,N'-diphenylurea is a minor by-product. These results are surprising in view of the discovery by Watanabe et al. that unsymmetric diaryl ureas cannot be prepared selectively from the reaction of aromatic formamides and aryl amines. With palladium and rhodium catalysts, the major product obtained was aniline, although some of the desired N-phenyl-N',N'-dibutylurea was obtained in each case. Carbamates may be prepared by the process of the invention if an alcohol is used as the trapping agent. As shown in Examples 7 and 8, formanilide reacts 1-hexanol with to give hexyl N-phenylcarbamate, while toluene-2,4-bisformamide reacts with 1-hexanol to give toluene-2,4-bis (hexyl carbamate).

3. The process of claim 1 wherein the primary formamide is a mono-, di-, or polyformamido derivative of benzene, toluene, diphenylmethane, poly(phenylmethylene), isophorone, or hexane.

4. The process of claim 1 wherein the alcohol has the structure R"OH in which R" is a $C_1$–$C_{30}$ linear, branched, or cyclic alkyl or aryl-substituted alkyl group.

5. The process of claim 1 wherein the Group VIII transition metal compound contains a metal selected from the group consisting of ruthenium, platinum, and rhodium.

6. The process of claim 1 wherein the process is performed at a temperature within the range of about 150° C. to about 200° C.

7. The process of claim 1 wherein the process is performed in the presence of an aromatic hydrocarbon solvent.

8. A selective process for making an aromatic carbamate, said process comprising reacting a primary aromatic formamide with a an alcohol in the presence of a Group VIII transition metal compound at a temperature greater than about 150° C. for a time sufficient to produce the aromatic carbamate.

9. The process of claim 8 wherein the primary aromatic formamide has the formula:

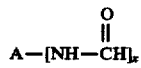

in which A is a $C_1$–$C_{30}$ aryl or alkyl-substituted aryl group, and x is an integer from 1 to 6.

10. The process of claim 8 wherein the primary aromatic formamide is a mono-, di-, or polyformamido derivative of benzene, toluene, diphenylmethane, or poly (phenylmethylene).

TABLE 1

| Synthesis of Isocyanate Precursors from Formamides | | | | | | |
|---|---|---|---|---|---|---|
| Ex # | Formamide | Amine/alcohol | Catalyst | Solvent* | Time (h) | % Conv. | Products (% Yield) |
| 1 | Formanilide | DBA | RuCl$_2$(PPh$_3$)$_3$ | mesitylene | 20 | 19 | DBPU (90), DPU (6) |
| 2 | Formanilide | DBA | RuCl$_2$(PPh$_3$)$_3$ | Ph$_2$CH$_2$ | 20 | 50 | DBPU (>90) |
| 3 | Formanilide | DBA | RuCl$_2$(PPh$_3$)$_3$ | Ph$_2$CH$_2$ | 6 | 75 | DBPU (85) |
| 4 | Formanilide | DBA | RuCl$_2$(DMSO)$_4$ | Ph$_2$CH$_2$ | 20 | 55 | DBPU (>90) |
| 5 | Formanilide | DBA | Pd(PPh$_3$)$_4$ | Ph$_2$CH$_2$ | 20 | 54 | DBPU (25), DPU (20), AN (40) |
| 6 | Formanilide | DBA | RhCl(CO)(PPh$_3$)$_3$ | Ph$_2$CH$_2$ | 20 | 18 | DBPU (10), DPU (5), AN (65) |
| 7 | Formanilide | n-hexanol | RuCl$_2$(PPh$_3$)$_3$ | — | 6 | 90 | PHC (50) |
| 8 | 2,4-TBF | n-hexanol | RuCl$_2$(PPh$_3$)$_3$ | — | 4 | 78 | TBHC (20) |

*All experiments run with 10 mL solvent, except #3, in which 2.5 mL solvent was used. N-hexanol served as the solvent for #7 and #8.
2,4-TBF = toluene-2,4-bis(formamide); DBA = di-n-butylamine
Products: DBPU = N,N-dibutyl-N'-phenylurea; DPU = N,N'-diphenylurea; PHC = N-phenylhexylcarbamate; AN = aniline; TBHC = Toluene-2,4-bis(n-hexylcarbamate)

I claim:

1. A selective process for making a carbamate, said process comprising reacting a primary formamide with an alcohol in the presence of a Group VIII transition metal compound at a temperature and for a time sufficient to produce the carbamate.

2. The process of claim 1 wherein the primary formamide has the formula:

in which A is a $C_1$–$C_{30}$ linear, branched, or cyclic alkyl, aryl, or aralkyl group, and x is an integer from 1 to 6.

11. The process of claim 8 wherein the alcohol has the structure R"OH in which R" is a $C_1$–$C_{30}$ linear, branched, or cyclic alkyl or aryl-substituted alkyl group.

12. The process of claim 8 wherein the Group VIII transition metal compound contains a metal selected from the group consisting of ruthenium, rhodium, and plantinum.

13. The process of claim 8 wherein the process is performed at a temperature within the range of about 150° C. to about 200° C.

14. The process of claim 8 wherein the process is performed in the presence of an aromatic hydrocarbon solvent.

* * * * *